(12) United States Patent
Park

(10) Patent No.: US 9,649,129 B2
(45) Date of Patent: May 16, 2017

(54) PERCUTANEOUS EXTRAFORAMINOTOMY WITH FORAMINAL LIGAMENT RESECTION AND INSTRUMENT TOOL USED FOR THE SAME

(71) Applicant: Kyung-Woo Park, Seoul (KR)

(72) Inventor: Kyung-Woo Park, Seoul (KR)

(73) Assignee: Kyung-Woo Park, Seoul (KR)

( * ) Notice: Subject to any disclaimer, the term of this patent is extended or adjusted under 35 U.S.C. 154(b) by 343 days.

(21) Appl. No.: 13/768,848

(22) Filed: Feb. 15, 2013

(65) Prior Publication Data

US 2014/0163598 A1    Jun. 12, 2014

(30) Foreign Application Priority Data

Dec. 11, 2012  (KR) .................. 10-2012-0143335

(51) Int. Cl.
A61B 17/34  (2006.01)
A61B 17/16  (2006.01)
(Continued)

(52) U.S. Cl.
CPC .......... *A61B 17/34* (2013.01); *A61B 17/1659* (2013.01); *A61B 17/1671* (2013.01);
(Continued)

(58) Field of Classification Search
CPC . A61B 17/34; A61B 17/1671; A61B 17/1659; A61B 17/3421;
(Continued)

(56) References Cited

U.S. PATENT DOCUMENTS 4,545,374 A * 10/1985 Jacobson ........... A61B 17/0218
                                                    600/210
4,573,448 A *  3/1986 Kambin ............. A61B 17/3417
                                                    128/898
(Continued)

FOREIGN PATENT DOCUMENTS

CN    2304368 Y    1/1999
CN    2348784 Y    11/1999
(Continued)

OTHER PUBLICATIONS

Epidural Lysis of Adhesions, New York Spine &Wellness Center, Nov. 15, 2005.*

(Continued)

*Primary Examiner* — Jonathan Miles
*Assistant Examiner* — Kankindi Rwego
(74) *Attorney, Agent, or Firm* — IP & T Group LLP

(57) ABSTRACT

Provided is a method for performing a percutaneous extraforaminotomy with foraminal ligament resection, which examines various ligaments around intervertebral foramen, artificially expands the intervertebral foramen blocked by adhesive fibrosis through repeated inflammatory reactions using epidural neurolysis or percutaneous extraforaminotomy, transmits chemical materials efficacious in pain treatment to the periphery of nervous branches causing pain through a catheter, and smoothly discharges an inflammatory material existing in spinal canal with the chemical materials through the intervertebral foramen.

5 Claims, 8 Drawing Sheets

(51) Int. Cl.
  *A61B 17/32* (2006.01)
  *A61B 17/3207* (2006.01)
  *A61B 17/22* (2006.01)

(52) U.S. Cl.
  CPC .............. *A61B 17/320016* (2013.01); *A61B 17/320708* (2013.01); *A61B 17/3421* (2013.01); *A61B 2017/1602* (2013.01); *A61B 2017/22082* (2013.01)

(58) Field of Classification Search
  CPC .... A61B 17/320016; A61B 17/320708; A61B 2017/1602; A61B 2017/22082; A61B 17/1664; A61B 17/1666; A61B 17/1668; A61B 17/1675; A61B 17/1682; A61B 17/1684; A61B 17/1686; A61B 17/320036; A61B 2017/320004; A61B 2017/320008
  See application file for complete search history.

(56) References Cited

U.S. PATENT DOCUMENTS

| | | | | |
|---|---|---|---|---|
| 2006/0276816 | A1* | 12/2006 | Eckman | A61B 17/32070 606/160 |
| 2008/0195084 | A1* | 8/2008 | Rinner | A61B 17/32070 606/1 |
| 2008/0216846 | A1* | 9/2008 | Levin | A61B 17/22 128/898 |
| 2011/0288553 | A1* | 11/2011 | Jansen | A61B 17/1671 606/83 |

FOREIGN PATENT DOCUMENTS

| | | |
|---|---|---|
| CN | 201022736 Y | 2/2008 |
| JP | 2002-500912 | 1/2002 |
| JP | 2003-531648 | 10/2003 |
| JP | 2008-260873 | 1/2010 |
| JP | 2010-502305 | 1/2010 |
| KR | 100627170 | 9/2006 |

OTHER PUBLICATIONS

Park, Hun K., et al. "Intervertebral foraminal ligaments of the lumbar spine: anatomy and biomechanics" Child's Nervous System 17.4-5 (2001):275-282.*

Office Action issued by the Japanese Patent Office on Mar. 28, 2014.

Min, Jun-Hong, et al., Anatomic Analysis of the Transforaminal Ligament in the Lumbar Intervertebral Foramen, Neurosurgery, Jul. 2005, pp. 37-41, vol. 57.

Final Rejection issued by the Japanese Patent Office on Oct. 21, 2015.

Office Action isused by the State Intellectual Property Office on Mar. 31, 2016.

* cited by examiner

PERCUTANEOUS EXTRAFORAMINOTOMY WITH FORAMINAL LIGAMENT RESECTION AND INSTRUMENT TOOL USED FOR THE SAME

CROSS-REFERENCE(S) TO RELATED APPLICATIONS

The present application claims priority of Korean Patent Application No(s). 10-2012-0143335, filed on Dec. 11, 2012. The disclosure of each of the foregoing applications is incorporated herein by reference in its entirety.

BACKGROUND OF THE INVENTION

The present invention relates to a method for performing a percutaneous extraforaminotomy with foraminal ligament resection, which is capable of relieving pain by discharging an inflammatory material existing in spinal canal through intervertebral foramen to the outside, and instrument tools used for the same, and more particularly, to a percutaneous extraforaminotomy with foraminal ligament resection, which expands the size of intervertebral foramen by resecting minute ligaments entangled in the intervertebral foramen through instrument tools such that a chemical material supplied to spinal canal through a catheter and an inflammatory material existing in the spinal canal are smoothly discharged to the outside through the intervertebral foramen, and instrument tools used for the same.

As of now, various articles have provided an anatomical description of the transforaminal ligaments of the lumbar spine and many authors have conducted the radiological analysis of the transforaminal ligaments. Even if the authors discussed the possible clinical implications of these ligaments, it is unclear what clinical implications of these ligaments are. In particular, the influence of TFL (transforaminal ligament) has been insignificant to the surgeons who focus on the mechanical factors such as disc bulging, ligament thickening, facet hypertrophy, and structural changes like stenosis and spondylolisthesis.

On the other hand, it is quite reasonable to presume that any situation which diminishes the size of the intervertebral foramen, such as stenosis or loss of intervertebral disc height, would increase the relative amount of area in the foramen occupied by the transforaminal ligaments. However, the study and analysis regarding the clinical significance of this is presently not sufficient.

This article—Jun-Hong Min, et. al. "anatomic analysis of the transforaminal ligament in the lumbar intervertebral foramen" operative neurosurgery Vol. 57:37~41, July 2005.—provides an anatomical description of the transforaminal ligaments of the lumbar spine. Although the importance of these structures is not yet clear, they may contribute to nerve root compression in certain cases. As such, they may contribute to persistent symptoms after more medical decompressive procedure. Spine surgeons should be aware of the presence of these structures and may consider them in the etiology of otherwise unexplained sciatic symptoms.

The article introduced above is an excellent and timely article in evaluating the anatomical analysis of the transforaminal ligaments of the lumbar intervertebral foramen, because the posterolateral approach is becoming more popular for the surgical treatment of lumbar far-lateral discs and foraminal stenosis.

Even if surgeons usually do not search for transforaminal ligaments during posterior foraminotomy, it is important and also useful for surgeons to have anatomical information in this area. It will be of great value and informative for neurosurgeons if the authors could conduct the radiological analysis of the transforaminal ligaments and study the correlation between anatomical and the surgical anatomy of the intervertebral foramen in the near future.

FIG. 1 is a view illustrating clinical anatomy of intervertebral foramen. The intervertebral foramen consists of spinal nerve (dorsal root ganglion), sinuvertebral nerves, veins (radicular vein, intervertebral veins), spinal artery, and ligaments.

FIG. 2 is a schematic diagram from the external aspect of intervertebral foramen. 1. Spinal artery, 2. Ventral ramus of spinal nerve, 3. Recurrent meningeal nerve, 4 and 5. Medial and lateral divisions of dorsal primary ramus, 6. Veins.

FIG. 3 is a view illustrating clinical anatomy of transforaminal ligament and FIG. 4 is a view illustrating a model image of lumbosacral spine.

As shown in FIG. 3, ligaments around the intervertebral foramen are categorized into four parts: ligaments of the entrance zone, ligaments of the mid-zone, ligaments of the exit zone, and ligaments of the post-canal zone. The ligaments of the entrance zone consist of posterior longitudinal ligament, Hoffmann ligament, and peridural membrane; the ligaments of the mid-zone include fascial condensations attaching the nerve root sleeve to the pedicles and ligamentum flavum; the ligaments of the exit zone (around intervertebral foramen) contain internal ligament, transforaminal ligament, and external ligament; and the ligament of the post-canal zone include lumbar cribriform fascia.

On the other hand, Amonoo-Kuofi et al. (1998a) J. Ant. 156, p 177~183 divided TFLs (transforaminal ligaments) into three categories: internal ligaments, intraforaminal ligaments, and external ligaments. The internal ligament group includes the oblique inferior TFL (transforaminal ligament); the intraforaminal ligament group includes the deep anterior intraforaminal ligament, the oblique superior TFL (transforaminal ligament), and the horizontal mid-TFL (transforaminal ligament); and the external ligament group contains the superior, middle, and inferior corporotransverse ligaments. However, a different classification is applied to the L5, S1 IVF (intervertebral foramen), as shown in FIG. 4. The L5, S1 IVF (intervertebral foramen) consists of four types of ligamentous structure: the lumbosacral ligament, the lumbosacral hood, the corpotransverse ligament, and the mamillo-transverso-accessory ligament.

FIG. 5 is a view illustrating clinical anatomy of ligament closing intervertebral foramen, which is different for each patient. A. Oblique inferior TFL, B. Anterior intraforaminal ligament, C. Oblique superior TFL, D. Mid-TFL, E. Superior and inferior corporotransverse ligament, and F. Corporotransverse ligament.

Role of the foraminal ligament in the induction of low back pain including sciatica is divided into two aspects: inflammatory aspect and mechanical aspect. In terms of the inflammatory aspect, low back pain is affected by a series of processes such as activation of fine and non-myelinated pain endings, release of proinflammatory cytokines, vasodilation and edema, and adhesive fibrosis. In terms of the mechanical aspect, the below conditions should be considered: periradicular fibrosis, malposition of the transarticular ligament (especially, superior and inferior corporotransverse ligament) due to acquired reduction of intervertebral disc height, ossification of foraminal ligament, anomalies of trunks and conjoint nerve root, and entrapment of dorsal root ganglia (L5: corporotransverse ligament, L1-L4: inferior corporotransverse ligament).

Whereas the chemical neurolysis is applied to the problems of the inflammatory aspect, the mechanical epidural neurolysis by caudal catheterization or percutaneous extraforaminotomy is used to solve the problems of the mechanical aspect.

Back pain is a very common symptom that most of people experience more than once for the whole life. It is known that from 70 to 80 percent among the patients with back pain can be improved through the conservative method without a special treatment. The cases accompanying sciatica among the patients with back pain amount to about from 13 to 40 percent. Pathophysiological reason of sciatica is divided into mechanical factor and biochemical factor. In point of fact, we have neurosurgically put emphasis on mechanical factors such as disc bulging, ligament thickening, and facet hypertrophy for the treatment of sciatica. That is, most of neurosurgeons have believed that mechanical problems such as disc herniation and spinal stenosis cause sciatica, much more back pain.

However, with the introduction of epidural neurolysis, the inflammatory reaction around the intervertebral foramen has been considered as a main reason of sciatica.

FIG. 6 is a schematic view illustrating an image for explaining the process of pain and nerve dysfunction. The process of pain and nerve dysfunction may be easily understood with reference to FIG. 6.

Step A: Activation of adhesion molecules in the endoneurial capillary by tumor necrosis factor (TNF)

Step B: 1) Adhesion of circulating white blood cells (WBC), 2) Extravasation of WBC, and 3) Aggregation of thrombocytes and formation of a thrombus Step C: 1) Local release of TNF, Myelin injury, Accumulation of Na-like channels, Induction of allodynia in dorsal root ganglion (DRG) and spinal cord, 2) Decreased blood flow and increased permeability nutritional deficit In other words, biochemical factors undetected by magnetic resonance imaging (MRI) such as insufficient blood supply to nerve, mild inflammation, and fibroblastic adhesion around intervertebral foramen is in more important position.

So far, however, the surgery for treating pain of disc patients has relied on neurosurgical treatment for mechanical factors rather than analysis of biochemical factors which are not checked by MRI.

SUMMARY OF THE INVENTION

An embodiment of the present invention is directed to a method for performing a percutaneous extraforaminotomy with foraminal ligament resection, which examines various ligaments around intervertebral foramen, artificially expands the intervertebral foramen blocked by adhesive fibrosis through repeated inflammatory reactions using epidural neurolysis or percutaneous extraforaminotomy, transmits chemical materials efficacious in pain treatment to the periphery of nervous branches causing pain through a catheter, and smoothly discharges an inflammatory material existing in spinal canal with the chemical materials through the intervertebral foramen.

Another embodiment of the present invention is directed to instrument tools which are effectively used for a method for performing a percutaneous extraforaminotomy.

In accordance with an embodiment of the present invention, a percutaneous extraforaminotomy with foraminal ligament resection includes: a first step of examining various ligaments around intervertebral foramen; a second step of deciding an insertion position of a trocar according to a ligament structure around the intervertebral foramen, which is different for each patient; a third step of inserting the trocar toward a target point for resection through the skin of facet joint adjacent to the intervertebral foramen; a fourth step of inserting the trocar into a cannula and then separating the trocar to secure a space for inserting subsequent tools; a fifth step of inserting an endmill into the cannula, turning the endmill to scratch ligaments attached to the facet joint, and detaching the scratched ligaments in the intervertebral foramen; a sixth step of separating the endmill from the cannula, inserting a curret into the cannula, additionally detaching the scratched ligaments attached to the facet joint, and scraping residue to expand the size of the intervertebral foramen; and a seven step of inserting a catheter into the intervertebral foramen to transmit a chemical material to the periphery of nervous branches causing pain, and discharging an inflammatory material existing in a spinal column and the intervertebral foramen with the chemical material through the intervertebral foramen.

The second step may include deciding a target for resection at the intervertebral foramen in the opposite side of a disc space connected to one side of the intervertebral foramen, and the third step may include checking the position of the trocar through an X-ray image device called C-ARM.

In accordance with another embodiment of the present invention, a percutaneous extraforaminotomy with foraminal ligament resection includes: a first step of examining various ligaments around intervertebral foramen; a second step of deciding an insertion position of a trocar according to a ligament structure around the intervertebral foramen, which is different for each patient; a third step of inserting a trocar toward a target point for resection through the skin of facet joint adjacent to the intervertebral foramen; a fourth step of inserting the trocar into a cannula and then separating the trocar to secure a space for inserting subsequent tools; and a fifth step of inserting an endoscope and laser into the cannula and removing ligaments through the laser while checking a target ligament through the endoscope with the naked eye.

In accordance with another embodiment of the present invention, there are provided instrument tools which are applied to a percutaneous extraforaminotomy with foraminal ligament resection. The instrument tools includes: a trocar inserted through the skin to intervertebral foramen so as to reach a intervertebral foramen resection target point (contacted with upper and lower facet joints) of a treatment zone; a cannula including a handle mounted at one end thereof and a sleeve extended from the handle and having a guide hole for inducing an instrument tool to be smoothly inserted toward a target ligament position, wherein the trocar is inserted into the cannula so as to reach the target point of the intervertebral foramen; an endmill including a handle mounted at one end thereof and a knife bladed tip integrated with a leading end thereof and inserted into the cannula so as to make a scratch for easily detaching minute ligaments blocking the intervertebral foramen from vital structures; and a curret inserted into the cannula and including a handle provided at one end thereof and a scraper tip provided at a leading end thereof so as to additionally detach the scratched ligaments attached to the facet joint and scrape residue.

BRIEF DESCRIPTION OF THE DRAWINGS

FIG. 8A is a side view illustrating a spine, FIG. 8B is a enlarged view of the dotted line portion and FIG. 8C is a schematic diagram illustrating the front view of FIG. 8A.

FIGS. 9 to 12 illustrate instrument tools used for the percutaneous extraforaminotomy with foraminal ligament resection according to the embodiment of the present invention. Here, FIG. 9 is a perspective view illustrating a trocar, FIG. 11 is a perspective view illustrating a endmill.

DESCRIPTION OF SPECIFIC EMBODIMENTS

Figure 1:
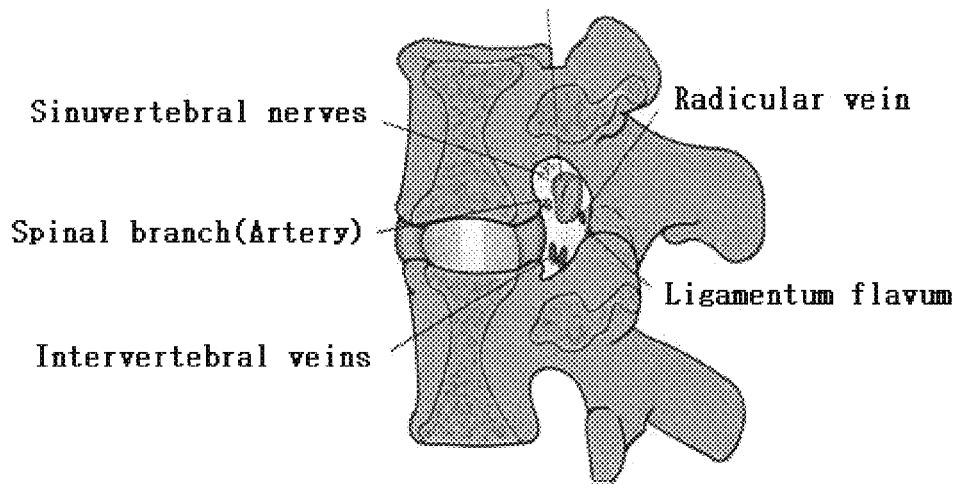
FIG. 1 is a view illustrating clinical anatomy of intervertebral foramen.
Figure 2:
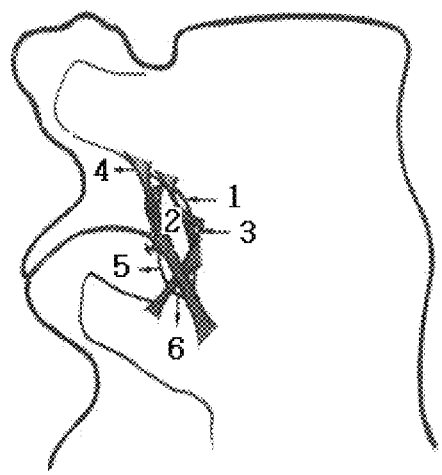
FIG. 2 is a schematic diagram from the external aspect of intervertebral foramen.
Figure 3:
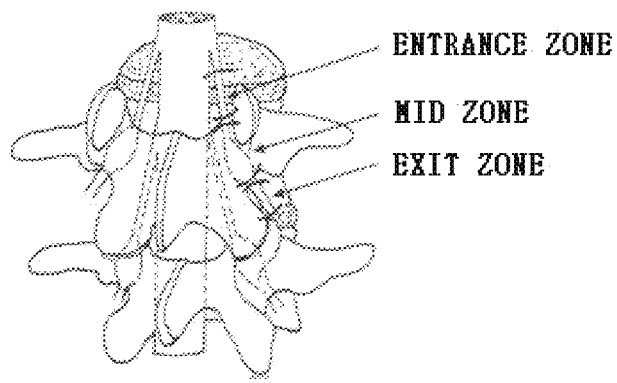
FIG. 3 is a view illustrating clinical anatomy of transforaminal ligament.

Exemplary embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various figures and embodiments of the present invention.

A percutaneous extraforaminotomy with foraminal ligament resection and instrument tools used for the same according to an embodiment of the present invention use chemical neurolysis in combination with mechanical neurolysis, in order to improve an effect of back pain treatment.

Before the embodiment of the present invention is described, the concept of the present invention will be described.

First, whereas the chemical neurolysis is applied to problems in terms of the inflammatory aspect, mechanical epidural neurolysis or percutaneous extraforaminotomy by caudal catheterization is used to solve problems in terms of the mechanical aspect.

The applicant of the present invention has taken an approach in terms of the inflammatory aspect in which back pain or sciatica is caused by adhesive fibroblast that is released from damaged disc (nucleus pulposus) and cartilage and then accumulated around TFL of intervertebral foramen. That is, the applicant of the present invention has analyzed the physiological reason of pain and target points of the inflammatory process in terms of the inflammatory aspect instead of the mechanical aspect. Furthermore, the applicant has clinically examined the anatomical structure of intervertebral foramen and TFL.

Furthermore, the applicant has determined that the clinical importance of the percutaneous extraforaminotomy with TFL resection would increase in terms of biochemical and inflammatory aspects.

According to the determination grounds, various ligaments around intervertebral foramen are examined, and the intervertebral foramen which is tightened and blocked by adhesive fibrosis through repeated inflammatory reactions needs to be mechanically expanded by epidural neurolysis or percutaneous extraforaminotomy. Then, chemical materials efficacious in pain treatment need to be properly transmitted to the periphery of nerve branches causing the pain. That is, when the mechanical neurolysis and the chemical neurolysis are used together, the effect of the treatment may be increased.

If spinal column and intervertebral foramen are compared to the structure of pump, intervertebral foramen corresponds to the pathway between a main column of the pump and an outlet of water. Intervertebral foramen is the pathway of nerve ganglion, blood vessel such as vein and artery, lymphatic vessel, and autonomic nervous system. Also, DRG (Dorsal Root Ganglion) vulnerable to shock and inflammation is located in this area and fine ligaments get entangled like a web, so that the derivatives by the inflammatory reaction in spinal column are accumulated in the intervertebral foramen. Thus, destructive reactions such as adhesion to nerve tissue and edema by inflammation and disturbance of blood flow to spinal column occur in this intervertebral foramen severely and frequently. Therefore, to solve the inflammation in the intervertebral foramen and decompress entrapment neuropathy or entrapped part of nerve is the key to the successful surgery.

Based on the above-described concept of the present invention, the percutaneous extraforaminotomy with foraminal ligament resection will be described as follows.

FIGS. 9 to 12 illustrate instrument tools used for the percutaneous extraforaminotomy with foraminal ligament resection according to the embodiment of the present invention.

Referring to the drawings, the instrument tools for ligament resection using percutaneous extraforaminotomy related to transforaminal ligament (TFL) according to the embodiment of the present invention includes four components consisting of a trocar, a cannula, an endmill, and a curret.

Figure 12A:
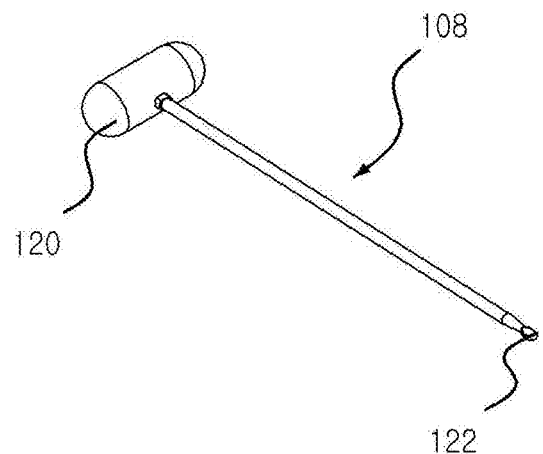
FIG. 12a is a perspective view illustrating a curret and FIG. 12B is a front view illustrating the curret.
Figure 12B:
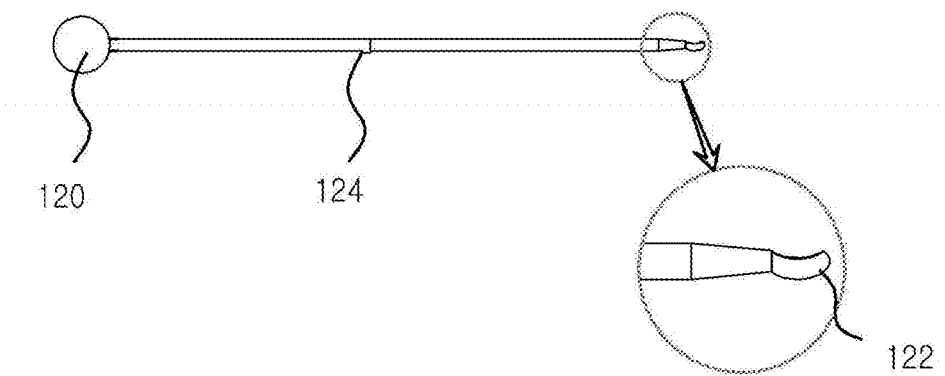

More specifically, the instrument tools include the trocar 102 (refer to FIG. 9), the cannula 104 (refer to FIGS. 10A and 10B), the endmill 106 (refer to FIG. 11), and the curret 108 (refer to FIGS. 12a and 12b). The trocar 102 is inserted through the skin to intervertebral foramen so as to reach an intervertebral foramen resection target point (contacted with upper and lower facet joints) of a treatment zone. The cannula 104 includes a handle 112 mounted at one end thereof and a sleeve 114 extended from the handle 112 and having a guide hole 114a for inducing the instrument tool to be smoothly inserted to a target ligament position. The trocar 102 is inserted into the cannula 104 so as to reach the resection target point of the intervertebral foramen. The endmill 106 includes a handle 116 mounted at one end thereof and a knife blade tip 118 integrated at a leading end thereof. The endmill 106 is inserted into the cannula 104 so as to make a scratch for easily detaching minute ligaments blocking the intervertebral foramen from vital structures. The curret 108 is inserted into the cannula 104 and includes a handle 120 mounted at one end thereof and a concave scraper tip 122 mounted at a leading end thereof. The curret 108 additionally detaches the scratched ligaments attached to facet joint and scrapes residue.

In this embodiment of the present invention, the trocar 102 has a thin and long probe shape so as to be smoothly inserted and to minimize the damage of vital structures around the target ligament.

The endmill 106 is used when resecting ligaments attached to the facet joint at the exit zone of the intervertebral foramen. The knife blade tip 118 of the endmill 106 has a spiral structure to easily and accurately perform resection. Furthermore, the knife blade tip 118 has a relatively dull edge to minimize the damage of vital structures around the target ligament.

The current 108 is used to precisely resect the transarticular ligaments tightening dorsal root ganglion (DRG), after the endmill 106 is used. The scraper tip 122 of the curret 108 has circumference formed in a round spoon head shape. Therefore, the scraper 122 may minimize the damage of vital structures positioned around the transarticular ligament during the resection. Furthermore, the scraper 122 resects the ligaments scratched by the endmill 106, scrapes the resected ligaments, and pushes the scraped ligaments to the outside of the intervertebral foramen.

In particular, the handle 120 of the curret 108 has an indicating protrusion 124 provided on the central portion thereof such that a surgeon may accurately recognize the direction of the spoon head. The indicating protrusion 124 serves to minimize a risk caused when a surgeon mistakes the direction of the spoon head.

When the instrument tool set having the above-described components is used to perform a surgery, biochemical medicine may smoothly permeate into the target position of the intervertebral foramen, compared to the conventional epidural block (injection). Furthermore, the transarticular ligament tightening the DRG of the intervertebral foramen may be effectively resected.

Referring to FIGS. 7 and 8A to 8C, the percutaneous extraforaminotomy with foraminal ligament resection using the instrument tool set will be described as follows.

Figure 5:
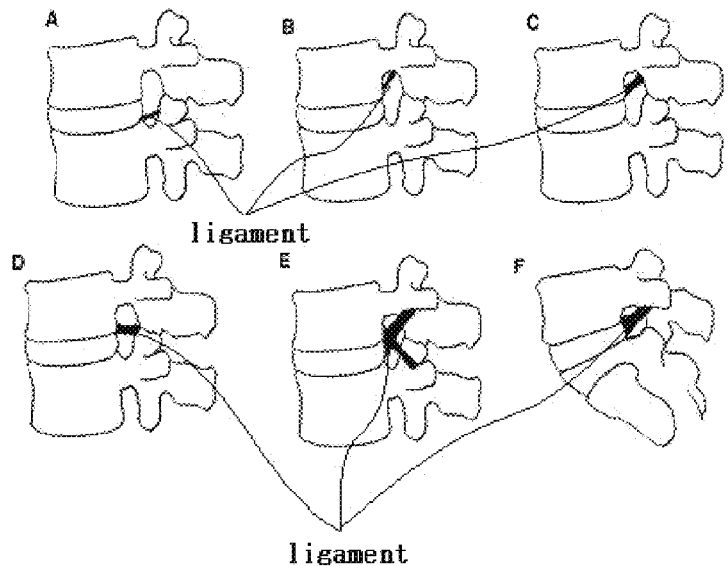
FIG. 5 is a view illustrating clinical anatomy of ligament closing intervertebral foramen, which is different for each patient.
Figure 6:
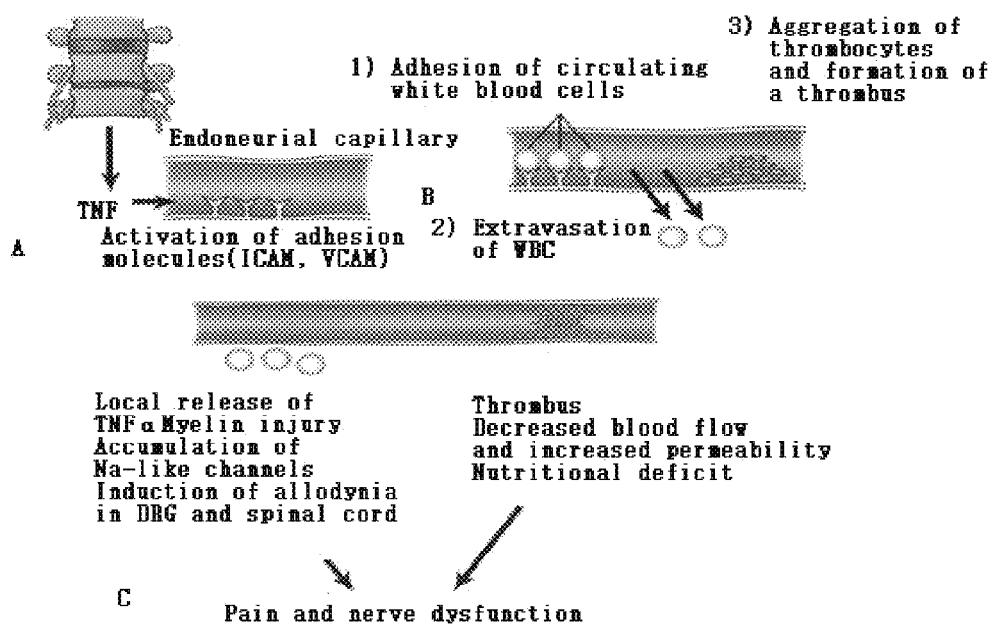
FIG. 6 is a schematic view illustrating an image for explaining the process of pain and nerve dysfunction.
Figure 7:
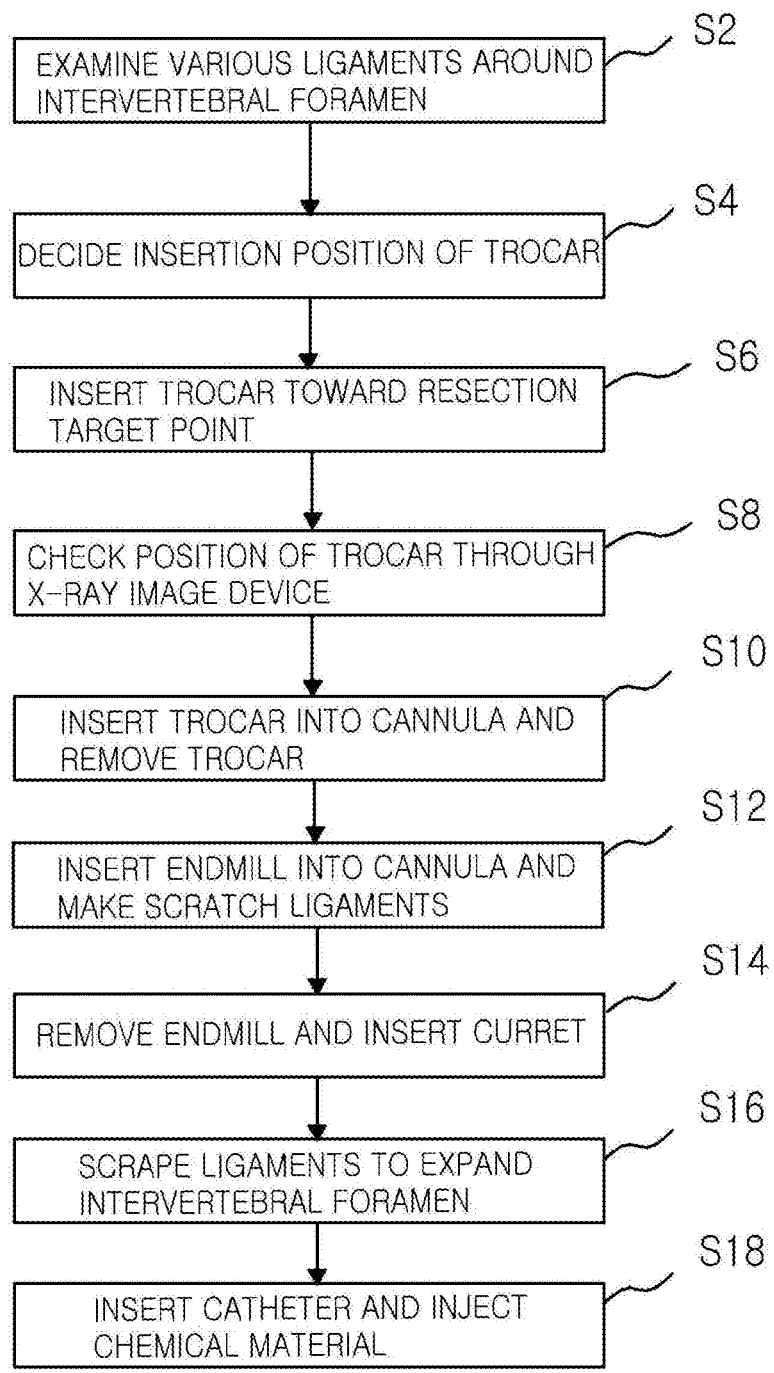
FIG. 7 is a flowchart showing a percutaneous extraforaminotomy with foraminal ligament resection according to an embodiment of the present invention.
Figure 8A:
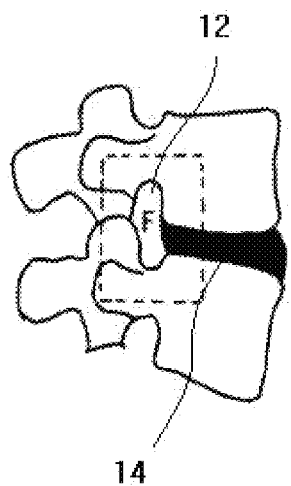
FIGS. 8A to 8C illustrate a resection target point at the initial stage of surgery for implementing the percutaneous extraforaminotomy with foraminal ligament resection according to the embodiment of the present invention. Here.
Figure 8B:
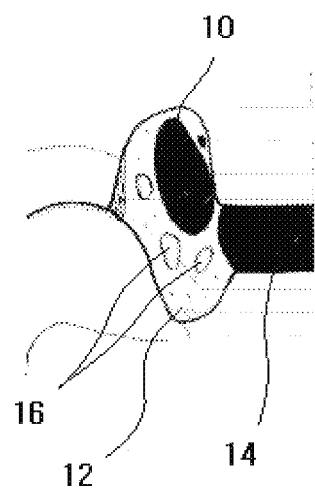
Figure 8C:
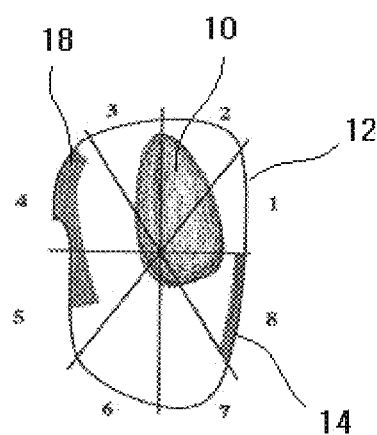
Figure 9:
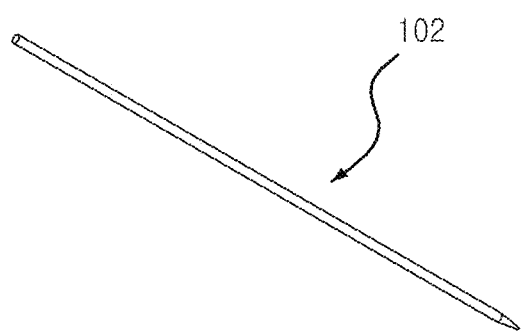
Figure 10A:
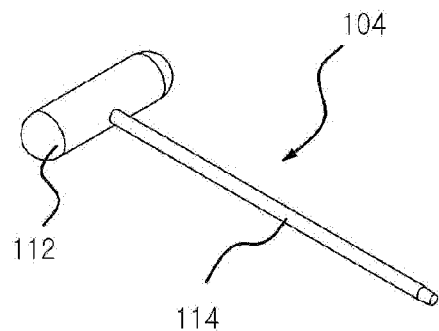
FIG. 10A is a perspective view illustrating a cannula.
Figure 10B:
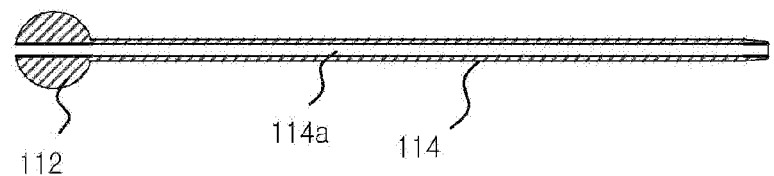
FIG. 10B is a front sectional view illustrating a cannula.
Figure 11:
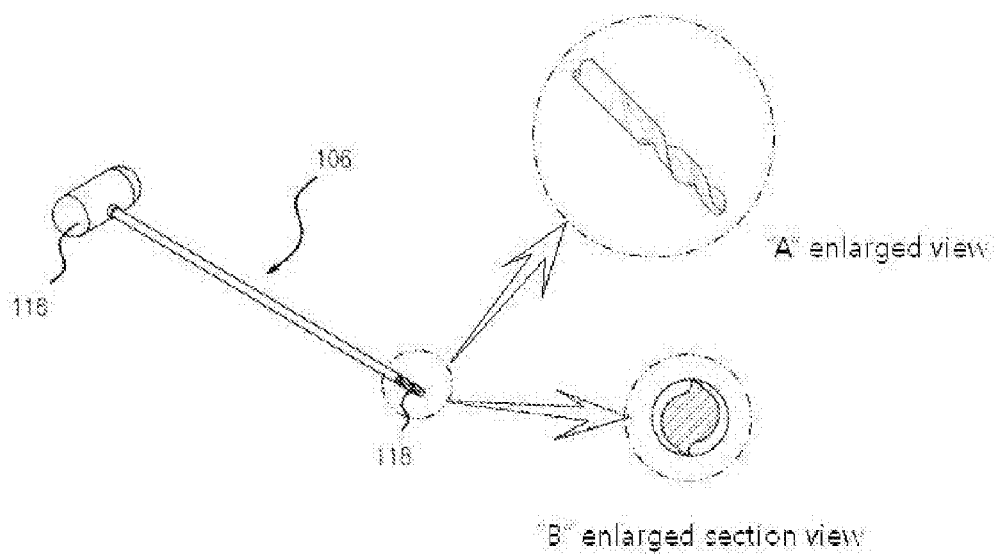

First, various ligaments around intervertebral foramen 12 are examined at step S2. At this time, the insertion position of the trocar is decided according to the ligament structure around the intervertebral foramen 12, which is different for each patient as illustrated in FIG. 5, at step S4. In this embodiment of the present invention, a target 18 for resection is decided at the intervertebral foramen in the opposite side of a disk space 14 connected to one side of the intervertebral foramen 12, as illustrated in FIGS. 8A and 8B. In this case, as illustrated in FIG. 8C, the edge of the intervertebral foramen becomes the target point, without being connected to the DRG 10. Reference numeral 16 represents the artery, vein, and autonomic nervous system.

Then, the trocar is inserted toward the target point through the skin of facet joint adjacent to the intervertebral foramen 12 at step S6. The position of the trocar is checked through an X-ray image device called C-ARM according to the ligament structure around the intervertebral foramen of the target point, at step S8.

The trocar is inserted into the cannula and then separated to secure a space for inserting a subsequent tool at step S10. The endmill is inserted into the cannula and then turned to scratch ligaments attached to the facet joint such that resection is easily performed in the intervertebral foramen, at step S12. The endmill is separated from the cannula, the curret is inserted to additionally detach the scratched ligament attached to the facet joint, and residue is scraped to expand the size of the intervertebral foramen, at steps S14 and 16.

Finally, a catheter is inserted into the intervertebral foramen to properly transmit a chemical material to the periphery of nervous branches causing pain, and an inflammatory material existing in the spinal canal with the chemical material is discharged through the intervertebral foramen, at step S18.

In another embodiment of the present invention, after steps S2 to S10 are performed, that is, after the cannula is inserted at step S10, an endoscope and laser may be inserted instead of the endmill and the curret, and ligaments may be removed by the laser while the target ligament is directly checked through the endoscope with the naked eyes.

In some patients with chronic low pain and lower extremity pain (sciatica) secondary to lumbar disc herniation and stenosis, severe adhesive fibroses around spinal canal and intervertebral foramen are accumulated, because of the synergy of inflammatory aspect and mechanical aspect. In this case, since severe adhesive fibroses prevent the catheter from advancing along the epidural space, it is difficult to apply the epidural neurolysis by caudal catheterization to the target region. Thus, the combination method of procedures of "the epidural neurolysis by caudal catheterization" and "percutaneous extraforaminotomy with foraminal ligament resection" is more effective for the treatment.

Figure 4:
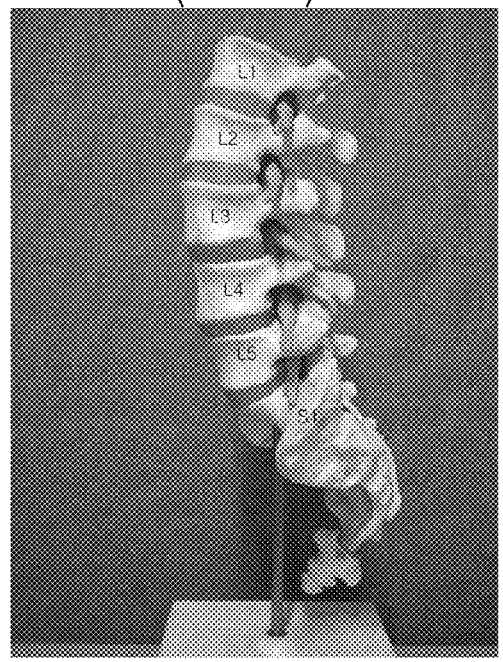
FIG. 4 is a view illustrating a model image of lumbosacral spine.

For the successful percutaneous extraforaminotomy, it is critical to determine the adequate target ligament for resection. That is, since intervertebral foramen contains various physiological structures such as nerve, blood vessel, indiscreet resection can make patients fall into a critical condition. Also, when it comes to the target ligament for resection, it should be considered separately according to the positions of spinal segments: L1-L4, L5 (refer to FIG. 4). In the case of the segments L1-L4, the target ligament for resection is transarticular ligament consisting of inferior and superior corporotransverse ligament and horizontal mid-transforaminal ligament. In the case of the segment L5, the target ligament for resection is transarticular ligament including lumbosacral hood and corporotransverse ligament. The target point for guide pin & percutaneous ligament resection is indicated as a "blue zone" (disc space (reference number 14)) and "red zone" (target space (reference number 18): inferior and superior corporotransverse ligament), as shown in FIG. 8C.

The reason to approach the target point for resection from the exit zone is that it is easy to access to the target (transarticular ligament) without the impairment of the other vital structure. That is, it is the best way to resect only the transarticular ligament entrapping DRG vulnerable to compression, without touching the ligament segmenting the other artery or vein.

According to the above-described embodiments, it is possible to obtain the following effects.

First, mechanical neurolysis and chemical neurolysis may be used together to increase the treatment effect.

Second, after the instrument tools are inserted toward the target point contacted with upper and lower facet joints so as to reach the target point of intervertebral foramen, ligaments are detached. Therefore, a pain relief surgery is easy to perform, blood is not discharged during the surgery, and recovery is fast after operation.

Third, when the endmill and the curret are inserted through the cannula, the dull edge of the endmill and the curret structure having the scraper tip having a spoon head shape may prevent the damage of muscle or other organs.

Fourth, the curret is used to detach the ligaments attached to the facet joint, and residue is scraped to expand the intervertebral foramen. Accordingly, the chemical material injected through the catheter and the inflammatory material may be discharged through the intervertebral foramen, and the blood vessel pressed by the ligaments may be expanded to smoothly circulate blood.

Fifth, unlike a surgical procedure which relieves pain only by injecting a chemical material through a catheter, the chemical material and the inflammatory material are discharged together to the outside of the intervertebral foramen. Accordingly, an excellent clinical effect may be acquired, and medicine may be sufficiently scattered around the nerve, thereby treating inflammatory factors.

While the present invention has been described with respect to the specific embodiments, it will be apparent to those skilled in the art that various changes and modifications may be made without departing from the spirit and scope of the invention as defined in the following claims.

What is claimed is:

1. A method for performing a percutaneous extraforaminotomy with foraminal ligament resection, comprising:
    a first step of examining various ligaments around intervertebral foramen;
    a second step of deciding an insertion position of a trocar according to a ligament structure around the intervertebral foramen;
    a third step of inserting the trocar toward a target point for resection through the skin of facet joint at an exit zone of the intervertebral foramen;
    a fourth step of inserting the trocar into a cannula and then separating the trocar to secure a space for inserting subsequent tools;
    a fifth step of inserting an endmill having a knife blade tip with a spiral structure into the cannula, turning the endmill to scratch ligaments attached to the facet joint, and detaching the scratched ligaments in the intervertebral foramen;
    a sixth step of separating the endmill from the cannula, inserting a curret into the cannula, additionally detaching the scratched ligaments attached to the facet joint, and scraping residue to expand the size of the intervertebral foramen; and
    a seventh step of inserting a catheter into the intervertebral foramen to transmit a chemical material to the periphery of nervous branches causing pain, and discharging an inflammatory material existing in a spinal column and the intervertebral foramen with the chemical material through the expanded intervertebral foramen.

2. The method for performing the percutaneous extraforaminotomy of claim 1, wherein the third step comprises checking the position of the trocar through an X-ray image device called C-ARM.

3. The method for performing the percutaneous extraforaminotomy of claim 1, wherein the second step comprises deciding that the target point for resection is at the intervertebral foramen in the opposite side of a disc space connected to one side of the intervertebral foramen.

4. A method for performing a percutaneous extraforaminotomy with foraminal ligament resection, comprising:
    a first step of examining various ligaments around intervertebral foramen;
    a second step of deciding an insertion position of a trocar according to a ligament structure around the intervertebral foramen;
    a third step of inserting a trocar toward a target ligament for resection through the skin of a facet joint at an exit zone of the intervertebral foramen, wherein the target ligament is a transarticular ligament including inferior and superior corporotransverse ligament and horizontal mid-transforaminal ligament, for spinal segments L1 to L4, and
    wherein the target ligament is a transarticular ligament including lumbosacral hood and corporotransverse ligament for spinal segment L5;
    a fourth step of inserting the trocar into a cannula and then separating the trocar to secure a space for inserting subsequent tools; and
    a fifth step of inserting an endoscope and laser into the cannula and removing the target ligament by the laser while checking the target ligament through the endoscope with the naked eye.

5. The method for performing a percutaneous extraforaminotomy with foraminal ligament resection of claim 1,
    wherein the target point for resection includes a target ligament,
    wherein the target ligament is a transarticular ligament including inferior and superior corporotransverse ligament and horizontal mid-transforaminal ligament, for spinal segments L1 to L4, and
    wherein the target ligament is a transarticular ligament including lumbosacral hood and corporotransverse ligament for spinal segment L5.

* * * * *

UNITED STATES PATENT AND TRADEMARK OFFICE
CERTIFICATE OF CORRECTION

PATENT NO. : 9,649,129 B2  
APPLICATION NO. : 13/768848  
DATED : May 16, 2017  
INVENTOR(S) : Kyung-Woo Park Page 1 of 1

It is certified that error appears in the above-identified patent and that said Letters Patent is hereby corrected as shown below:

Change the Title section as follows:
(54) METHOD FOR PERFORMING PERCUTANEOUS EXTRAFORAMINOTOMY WITH FORAMINAL LIGAMENT RESECTION AND INSTRUMENT TOOL USED FOR THE SAME Signed and Sealed this
Eighth Day of May, 2018

Andrei Iancu
*Director of the United States Patent and Trademark Office*